United States Patent
Xu et al.

(10) Patent No.: US 9,695,125 B2
(45) Date of Patent: Jul. 4, 2017

(54) METHOD FOR SYNTHESIZING CATIONIC BLEACH ACTIVATORS VIA A SINGLE-BATH REACTION

(71) Applicants: Changhai Xu, Wuxi (CN); Chang Sun, Wuxi (CN); Jinmei Du, Wuxi (CN); Shuangshuang Cui, Wuxi (CN); Jingjing Zhang, Wuxi (CN); Jiao Yu, Wuxi (CN); Zhiyong Huang, Wuxi (CN); Wenjuan Tang, Wuxi (CN); Yan Zhang, Wuxi (CN); Wenhua Chen, Wuxi (CN)

(72) Inventors: Changhai Xu, Wuxi (CN); Chang Sun, Wuxi (CN); Jinmei Du, Wuxi (CN); Shuangshuang Cui, Wuxi (CN); Jingjing Zhang, Wuxi (CN); Jiao Yu, Wuxi (CN); Zhiyong Huang, Wuxi (CN); Wenjuan Tang, Wuxi (CN); Yan Zhang, Wuxi (CN); Wenhua Chen, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 0 days.

(21) Appl. No.: 14/953,812

(22) Filed: Nov. 30, 2015

(65) Prior Publication Data

US 2016/0221955 A1 Aug. 4, 2016

(30) Foreign Application Priority Data

Jan. 30, 2015 (CN) .......................... 2015 1 0051139

(51) Int. Cl.
*C07D 225/02* (2006.01)
*C07D 207/26* (2006.01)
*C07D 211/76* (2006.01)
*C07D 223/10* (2006.01)

(52) U.S. Cl.
CPC ......... *C07D 225/02* (2013.01); *C07D 207/26* (2013.01); *C07D 211/76* (2013.01); *C07D 223/10* (2013.01)

(58) Field of Classification Search
CPC ............................ C07D 225/02; C07D 207/26
See application file for complete search history.

(56) References Cited

U.S. PATENT DOCUMENTS 7,179,779 B1 * 2/2007 Hauser ................ C11D 3/3915
252/186.29
9,228,294 B2 * 1/2016 Xu .......................... C11D 3/28

OTHER PUBLICATIONS

Ren et al (2013):STN International, HCAPLUS database (Columbus, Ohio), Accession No. 2013: 62615.*

* cited by examiner

*Primary Examiner* — Golam M M Shameem
(74) *Attorney, Agent, or Firm* — Lili Chen

(57) ABSTRACT

The present invention provides a method for synthesizing cationic bleach activators via a single-bath reaction, comprising steps of: separately dissolving 4-chloromethylbenoyl chloride and lactam in its respective solvent, adding an acid-binding agent to the lactam solution, next adding dropwisely 4-chloromethylbenoyl chloride solution into the lactam/acid binding-agent solution, and finally adding tertiary amine to the solution above to make a reaction solution, which is further treated with mixing and refluxing. The washed and dried final product is TBLC cationic bleach activator. The method of the present invention greatly simplifies the synthesizing process and lowers the stringency of reaction conditions for preparing cationic bleach activators (TBLC). At the same time, the present method produces TBLC cationic bleach activators with high yields, making it a suitable option for industrial production of these bleach activators.

8 Claims, No Drawings

METHOD FOR SYNTHESIZING CATIONIC BLEACH ACTIVATORS VIA A SINGLE-BATH REACTION

CROSS-REFERENCES AND RELATED APPLICATIONS

This application claims the benefit of priority to Chinese Application No. 201510051139.3, entitled "A method for synthesizing cationic bleach activators via a single-bath reaction", filed Jan. 30, 2015, which is herein incorporated by reference in its entirety.

BACKGROUND OF THE INVENTION

Field of the Invention

This invention belongs to the field of fine chemicals, in particular, the invention relates to methods and applications for synthesizing cationic bleach activators via a single-bath reaction.

Description of the Related Art

Hydrogen peroxide is a widely used bleacher in industry because of its environment-friendly and pollution-free properties. However, traditional bleaching methods of hydrogen peroxide have many shortcomings that limit their widespread application. Nowadays, there is a new bleaching method that uses hydrogen peroxide at lower temperatures. Compared with traditional methods, the new bleaching method is applied in nearly neutral environment (pH 11-12 in traditional methods by adding sodium hydroxide or sodium carbonate) and room or moderate temperature (about 100° C. in traditional methods). The new method has obvious advantages over the traditional ones, such as reducing the consumption of energy resources, lightening the workload on treatment of waste water, and decreasing the damage to bleaching substrates.

Bleach activators play an important role in the system of low-temperature bleaching. As an organic peroxy acid precursor, the bleach activator reacts with hydrogen peroxide in aqueous solution and produces peroxy acid which is more active than hydrogen peroxide, and can effectively eliminate colored impurities at a lower temperature. Sodium nonanoyloxy benzene sulfonate (NOBS), tetraacetylethylenediamine (TAED) and N-[4-(triethylammoniomethyl)benzoyl]lactam chloride (TBLC) are activators widely used during the bleaching process. However, the application of NOBS and TAED is limited because of some disadvantages such as side effects at near-neutral pH (e.g. NOBS) and low solubility (e.g. TAED). In contrast, TBLC has no disadvantages stated above. The optimum pH of TBLC is 7.2, and solubility of TBLC is excellent. At the same time, the quaternary ammonium salt cationic group of TBLC provides good affinity to negatively charged cellulosic fibers in aqueous solutions, which is helpful for enhancing the bleaching performance. However, high production cost and complex manufacture procedures are the main reasons impeding current application of TBLC in the industry. As for studies on TBLC like activators, many researchers are focusing on optimizing structures of the activators or modifying the bleaching procedures, for example, changing the carbon number of lactam loop of TBLC in order to increase hydrolytic stability or changing the structure of quaternary ammonium salt cationic group to synthesize activators of different or specific structures (e.g. dicationic structure) to investigate their application properties. Researchers found that the bleaching effect of (TBCC)—$H_2O_2$—$NaHCO_3$ at 60° C. is similar to that of $H_2O_2$—$NaHCO_3$ bleaching system at 90° C. In addition, the TBCC—$H_2O_2$—$NaHCO_3$ bleaching system can improve hygroscopicity of cotton fabrics. However, there are few researches on simplification of the TBLC synthesizing process to decrease the production cost and expand the application scope.

Therefore, there is a need in finding simplified methods for synthesizing TBLC. The present invention satisfies such a need and provides other advantages as well.

DETAILED DESCRIPTION

The present invention provides a method for synthesizing cationic bleach activators via a single-bath reaction, which greatly simplifies the TBLC synthesizing process. The technical scheme of the invention is as follows.

The present invention provides a single-bath method for synthesizing TBLC cationic bleach activators, comprising steps of:

1) separately dissolving 4-chloromethylbenoyl chloride and caprolactam in its respective solvent; and adding an acid-binding agent into the caprolactam solution to obtain a caprolactam/acid-binding agent solution;

2) adding drop-by-drop 4-chloromethylbenoyl chloride solution obtained in step 1) into the caprolactam/acid-binding agent solution, and preparing a caprolactam/acid-binding agent/4-chloromethylbenoyl chloride solution by stirring the mixture at room temperature;

3) adding tertiary amine into the caprolactam/acid-binding agent/4-chloromethylbenoyl chloride solution to make a reaction solution, and further treating the reaction solution with stirring and refluxing;

4) filtrating and evaporating the reaction solution in step 3) to obtain a dry solid of the cationic bleach activator. The final product is obtained by washing the dry solid of the cationic bleach activator.

In a preferred embodiment, the molar ratio of the tertiary amine, the 4-chloromethylbenzoyl chloride and the caprolactam in the reaction solution is 1:1:1.

In a preferred embodiment, the solvent used in step 1) is methylbenzene, furanidine, acetic ether, acetonitrile, ethanol or methanol. The acid binding agent is one or more reagents selected from sodium carbonate, potassium carbonate, sodium hydroxide, potassium hydroxide, triethylamine or N-methylmorpholine. The molar ratio of the acid binding agent to the 4-chloromethylbenzoyl chloride is 1:1 to 2:1.

In a preferred embodiment, the duration of the stirring at room temperature in step 2) is 3 hours.

In a preferred embodiment, the duration of the refluxing and stirring in step 3) is 4 hours.

In a preferred embodiment, the solvent used for washing is acetone; and the obtained cationic bleach activator has general structural formula as follows:

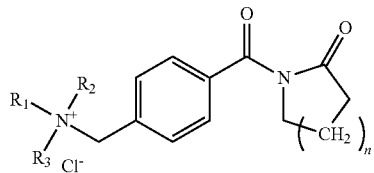

wherein n is 1, 2, 3, 4 or 5; the carbon number of alkyl group $R_1$, $R_2$, $R_3$ is 1, 2, 4, 6, 8, 10, 12, 14 or 16.

In a preferred embodiment, a method for synthesizing cationic bleach activators via a single-bath reaction comprises the steps of:

1) separately dissolving equal molar 4-chloromethylbenzoyl chloride and caprolactam in acetonitrile and adding trimethylamine, an acid-binding agent, to the caprolactam solution at a molar ratio of 2:1 to 1:1 (trimethylamine:4-chloromethylbenzoyl chloride);
2) adding drop-by-drop the 4-chloromethylbenzoyl chloride solution obtained in step 1) into the caprolactam-trimethylamine solution, and preparing a caprolactam-trimethylamine-4-chloromethylbenoyl chloride solution by stirring the mixture at room temperature for 3 hours;
3) adding tertiary amine into the caprolactam-trimethylamine-4-chloromethylbenoyl chloride solution with a molar ratio of 1:1:1 (tertiary amine:4-chloromethylbenzoyl chloride:caprolactam) to obtain a reaction solution; further treating the reacted solution with refluxing and stirring for 4 hours;
4) filtrating and evaporating the reacted solution to obtain a dry solid product, and washing the solid product with acetone to remove impurities and obtain the final product of cationic bleach activators. The final product of cationic bleach activators has structural formula as follows:

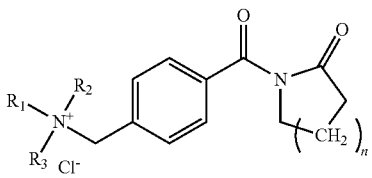

wherein n is 1, 2, 3, 4 or 5; the carbon number of alkyl group $R_1$, $R_2$, $R_3$ is 1, 2, 4, 6, 8, 10, 12, 14 or 16. People with ordinary skills in the art should know the routine methods for adjusting the carbon number of alkyl group for hydrophilic-lipophilic balance of cationic bleach activators.

The present invention provides a method for preparing cationic bleach activators, preferably TBLC-like cationic bleach activators.

The present invention has the following advantages. The traditional methods for synthesizing cationic bleach activator TBLC usually involve multi-bath reactions. The synthesizing procedures are complex and experimental conditions are strict and tough. The present invention provides a single-bath reaction method for synthesizing cationic bleach activator TBLC, which greatly simplifies the synthesizing procedure and significantly reduces the manufacture cost. For example, compared with multi-bath traditional methods for producing TBCC, the chemical yield of the present invention increases from 58% to 94.7%, and the production cost decreases from 1006.01 RMB/kg to 598.20 RMB/kg.

EXAMPLES

The following examples are provided for illustration purposes only, are not intended to limit the scope of the invention, which is limited only by the claims.

The materials, agents, apparatus and methods used in following examples, if not specially stated otherwise, are commonly available materials, agents, apparatus and known methods in the art.

Example 1

2.26 g (0.02 mol) caprolactam was dissolved with 20 mL acetonitrile, and 4.20 g (0.04 mol) sodium carbonate was added into the caprolactam solution. 3.86 g (0.02 mol) 4-chloromethylbenzoyl chloride was dissolved with 20 mL acetonitrile, and the 4-chloromethylbenzoyl chloride solution was added dropwisely into the caprolactam/sodium carbonate solution. The mixed solution was stirred for 3 hours at room temperature. 2.02 g (0.02 mol) triethylamine was added into the mixed solution to obtain a reaction solution, which was refluxed and stirred for 4 hours. Then the reaction solution was filtered, and the filtrate was evaporated by distillation to obtain a dry solid product. 20 mL acetone was used for washing the solid product with stirring under heated condition. After filtration and desiccation of the acetone-washed product, 6.45 g of white solid (final product) was obtained with a chemical yield of 88%. The NMR and MS data of the final product are as follows:

$^1$H-NMR (400 MHz, CDCl$_3$) δ 7.72-7.54 (m, 4H), 4.97 (s, 2H), 4.02-3.95 (m, 2H), 3.52-3.41 (m, 6H), 3.21-3.07 (m, 6H), 2.71-2.68 (m, 2H), 1.99-1.93 (m, 6H), 1.47-1.39 (m, 18H). MS-ESI (m/z): [M]$^+$ calculated for C$_{20}$H$_{31}$N$_2$O$_2$ [M-Cl]$^+$ is 331.2, and the experimentally determined value is 331.2.

Example 2

2.26 g (0.02 mol) caprolactam was dissolved with 20 mL acetonitrile, and 2.02 g (0.02 mol) triethylamine was added into the caprolactam solution. 3.86 g (0.02 mol) 4-chloromethylbenzoyl chloride was dissolved with 20 mL acetonitrile, and the 4-chloromethylbenzoyl chloride solution was added dropwisely into the caprolactam/triethylamine solution. The mixed solution was stirred for 3 hours at room temperature. 2.02 g (0.02 mol) triethylamine was added into the mixed solution above to obtain a reaction solution, which was refluxed and stirred for 4 hours. Then the reaction solution was filtered, and the filtrate was evaporated by distillation to obtain a dry solid product. 20 mL acetone was used for washing the solid product with stirring under heated condition. After filtration and desiccation of the acetone-washed solid product, 6.81 g of white solid (final product) is obtained with a chemical yield of 93%.

Example 3

2.26 g (0.02 mol) caprolactam was dissolved with 20 mL acetonitrile, and 2.02 g (0.02 mol) sodium carbonate was added into the caprolactam solution. 3.86 g (0.02 mol) 4-chloromethylbenzoyl chloride was dissolved with 20 mL acetonitrile, and the 4-chloromethylbenzoyl chloride solution was added drop-by-drop into the caprolactam/sodium carbonate solution. The mixed solution was stirred for 3 hour at room temperature. 1.46 g (0.02 mol) tert-Butylamine was added into the mixed solution above to make a reaction solution, which was refluxed and stirred for 4 hours. Then the reaction solution was filtered, and the filtrate was evaporated by distillation to obtain a dry solid production. 20 mL acetone was used for washing the solid product with stirring under heated condition. After filtration and desiccation of acetone-washed solid product, 5.56 g of white solid (final product) was obtained with a chemical yield of 91.7%. The NMR and MS data of the final product are as follows:

$^1$H NMR (400 MHz, CDCl$_3$): δ 7.74 (d, J=8.1 Hz, 2H), 7.52 (d, J=8.1 Hz, 2H), 5.08 (s, 2H), 3.96 (s, 2H), 3.62 (q, J=7.2 Hz, 2H), 3.18 (s, 6H), 2.66 (d, J=6.4 Hz, 2H), 1.82 (s, 6H), 1.39 (t, J=7.2 Hz, 3H); $^{13}$C NMR (100 MHz, CDCl$_3$): δ 177.6, 172.8, 138.5, 133.0, 130.2, 127.7, 65.9, 59.2, 48.8, 44.8, 38.6, 29.2, 28.9, 23.5, 8.4; MS-ESI (m/z): [M]$^+$ calculated for C$_{18}$H$_{27}$N$_2$O$_2$ is 303.2, and the experimentally determined value is 303.1.

Example 4

2.26 g (0.02 mol) caprolactam was dissolved with 20 mL acetonitrile, and 2.02 g (0.02 mol) sodium carbonate was added into the caprolactam solution. 3.86 g (0.02 mol) 4-chloromethylbenzoyl chloride was dissolved with 20 mL acetonitrile, and the 4-chloromethylbenzoyl chloride solution was added drop-by-drop into caprolactam/sodium carbonate solution. The mixed solution was stirred for 3 hours at room temperature. 2.02 g (0.02 mol) N,N-Dimethylbutylamine was added into the mixed solution to obtain a reaction solution, which was refluxed and stirred for 4 hours. Then the reaction solution was filtered, and the filtrate was evaporated by distillation to obtain a dry solid production. 20 mL acetone was used for washing the solid product with stirring under heated condition. After filtration and desiccation of acetone-washed product, 5.43 g of white solid (final product) was obtained with a chemical yield of 82%. The NMR and MS data of the final product are as follows:

$^1$H NMR (400 MHz, CDCl$_3$): δ 7.72 (d, J=8.1 Hz, 2H), 7.52 (d, J=8.1 Hz, 2H), 5.07 (s, 2H), 3.96 (s, 2H), 3.54-3.38 (m, 2H), 3.21 (s, 6H), 2.66 (d, J=6.3 Hz, 2H), 1.82 (s, 6H), 1.75 (s, 2H), 1.36 (dd, J=14.8, 7.4 Hz, 2H), 0.94 (t, J=7.3 Hz, 3H); $^{13}$C NMR (100 MHz, CDCl$_3$): δ177.8, 173.0, 138.7, 133.2, 130.3, 127.9, 66.6, 63.5, 49.6, 45.0, 38.7, 29.4, 29.0, 24.5, 23.6, 19.6, 13.7; MS-ESI (m/z): [M]$^+$ calculated for C$_{20}$H$_{31}$N$_2$O$_2$ is 331.2, and experimentally determined value is 331.1.

Example 5

2.26 g (0.02 mol) caprolactam was dissolved with 20 mL acetonitrile, and 2.02 g (0.02 mol) sodium carbonate was added into the caprolactam solution. 3.86 g (0.02 mol) 4-chloromethylbenzoyl chloride was dissolved with 20 mL acetonitrile, and the 4-chloromethylbenzoyl chloride solution was added drop-by-drop into the caprolactam/sodium carbonate solution. The mixed solution was stirred for 3 hours at room temperature. 2.02 g (0.02 mol) N,N-dimethylhexylamine was added into the mixed solution to obtain a reaction solution, which was refluxed and stirred for 4 hours. Then the reaction solution was filtered, and the filtrate was evaporated by distillation to obtain a dry solid product. 20 mL acetone was used for washing the solid product with stirring under heated condition. After filtration and desiccation of the acetone-washed product, 6.39 g of white solid (final product') was obtained with a chemical yield of 89%. The NMR and MS data of the final product are as follows:

$^1$H NMR (400 MHz, CDCl$_3$): δ 7.73 (d, J=8.1 Hz, 2H), 7.52 (d, J=8.1 Hz, 2H), 5.12 (s, 2H), 3.95 (s, 2H), 3.5-3.33 (m, 2H), 3.23 (s, 6H), 2.66 (d, J=6.4 Hz, 2H), 1.82 (s, 6H), 1.75 (s, 2H), 1.27 (d, J=10.0 Hz, 6H), 0.84 (t, J=6.8 Hz, 3H); $^{13}$C NMR (100 MHz, CDCl$_3$): δ 177.7, 172.9, 138.9, 133.2, 130.2, 127.9, 66.5, 63.8, 49.6, 45.0, 38.8, 31.3, 29.4, 29.1, 25.9, 23.7, 22.8, 22.3, 13.9; MS-ESI (m/z): [M]$^+$ calculated for C$_{22}$H$_{35}$N$_2$O$_2$ is 359.3, and the experimentally determined value is 359.1.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for synthesizing cationic bleach activators via a single-bath reaction, comprising steps of:
   1). separately dissolving 4-chloromethylbenoyl chloride and caprolactam in its respective solvent, and adding an acid-binding agent into the caprolactam solution to obtain a caprolactam/acid-binding agent solution;
   2). adding drop-by-drop the 4-chloromethylbenoyl chloride solution obtained in step 1) into the caprolactam/acid-binding agent solution, and stirring the mixture at room temperature to prepare a caprolactam/acid-binding agent/4-chloromethylbenoyl chloride solution;
   3). adding tertiary amine into the caprolactam/acid-binding agent/4-chloromethylbenoyl chloride solution to make a reaction solution, and further treating the reaction solution with stirring and refluxing; and
   4). filtrating and evaporating the reaction solution in step 3) to obtain a dry solid product of cationic bleach activators, and washing the dry solid product with a washing solvent to obtain a final product of cationic bleach activators.

2. The method of claim 1, wherein the molar ratio of the tertiary amine, the 4-chloromethylbenzoyl chloride and the caprolactam is 1:1:1.

3. The method of claim 1, wherein the solvent used in step 1) is methylbenzene, furanidine, acetic ether, acetonitrile, ethanol or methanol.

4. The method of claim 1, wherein the acid-binding agent used in step 1) is one to six reagents selected from the group consisting of potassium carbonate, sodium carbonate, potassium hydroxide, sodium hydroxide, triethylamine and methylmorpholine; and wherein the molar ratio of the acid-binding agent and 4-chloromethylbenzoyl chloride is 1:1 to 2:1.

5. The method of claim 1, wherein the stirring in step 2) is performed at room temperature for 3 hours.

6. The method of claim 1, wherein the duration of the refluxing and stirring in step 3) is 4 hours.

7. The method of claim 1, wherein the washing solvent is acetone; and wherein the obtained cationic bleach activators have a general structural formula as follows:

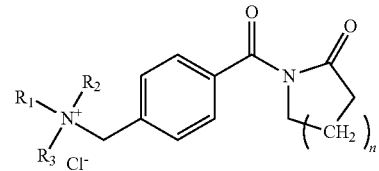

wherein n is 1, 2, 3, 4 or 5; the carbon number of alkyl group R$_1$, R$_2$, R$_3$ is 1, 2, 4, 6, 8, 10, 12, 14 or 16.

8. The method of claim 1, comprising the steps of:
   1). separately dissolving equal molar 4-chloromethylbenzoyl chloride and caprolactam in acetonitrile and adding trimethylamine, an acid-binding agent, to the caprolactam solution at a molar ratio of 2:1 to 1:1 (trimethylamine:4-chloromethylbenzoyl chloride);
   2). adding drop-by-drop the 4-chloromethylbenzoyl chloride solution obtained in step 1) into the caprolactam-trimethylamine solution, and stirring the mixture at room temperature for 3 hours to preparing a caprolactam/trimethylamine/4-chloromethylbenoyl chloride solution;
   3) adding tertiary amine into the caprolactam-trimethylamine-4-chloromethylbenzoyl chloride solution with a molar ratio of 1:1:1 (tertiary amine:4-chloromethylbenzoyl chloride:caprolactam) to obtain a reaction solution; and further treating the reacted solution with refluxing and stirring for 4 hours;

4) filtrating and evaporating the reacted solution to obtain a dry solid product, and washing the solid product with acetone and obtain a final product of cationic bleach activators, wherein the final product of cationic bleach activators has structural formula as follows:

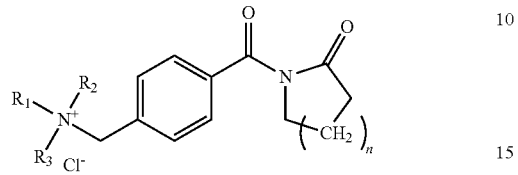

wherein n is 1, 2, 3, 4 or 5; the carbon number of alkyl group $R_1$, $R_2$, $R_3$ is 1, 2, 4, 6, 8, 10, 12, 14 or 16.

* * * * *